United States Patent [19]

Lidgren

[11] Patent Number: 4,721,390

[45] Date of Patent: Jan. 26, 1988

[54] METHOD FOR PRODUCING BONE CEMENT FOR FIXING PROSTHESES AND DEVICE FOR CARRYING OUT SAID METHOD

[75] Inventor: Lars A. A. Lidgren, Lund, Sweden

[73] Assignee: Mit AB, Sjobo, Sweden

[21] Appl. No.: 788,743

[22] Filed: Oct. 17, 1985

[30] Foreign Application Priority Data

Oct. 19, 1984 [SE] Sweden .............................. 8405232

[51] Int. Cl.⁴ .............................................. B01F 13/06
[52] U.S. Cl. ..................................... 366/139; 422/225
[58] Field of Search ................. 366/139; 422/99, 104, 422/225

[56] References Cited

U.S. PATENT DOCUMENTS

| | | |
|---|---|---|
| 3,640,510 | 2/1972 | Lea ........................................ 366/139 |
| 4,185,072 | 1/1980 | Puderbaugh et al. ........... 366/139 X |
| 4,277,184 | 7/1981 | Solomon .......................... 366/139 X |

FOREIGN PATENT DOCUMENTS

| | | |
|---|---|---|
| 36-3886 | 2/1961 | Japan . |
| 50-37950 | 12/1975 | Japan . |
| 56-45615 | 10/1981 | Japan . |
| 56-161044 | 12/1981 | Japan . |
| 8403830 | 4/1984 | PCT Int'l Appl. . |

Primary Examiner—Peter Nerbun
Attorney, Agent, or Firm—Schwartz, Jeffery, Schwaab, Mack, Blumenthal & Evans

[57] ABSTRACT

The present invention relates to a method for producing bone cement for fixing protheses, whereby the bone cement is manufactured by mixing various substances with each other to provide a setting mass which in set condition is adapted to fix prostheses at surrounding bone tissue. In order to prevent large amounts of air from being stirring into the mixture, mixing of said various substances occurs under vacuum. The invention also relates to a device for carrying out the method for producing bone cement for fixing prostheses, whereby the bone cement is manufactured by mixing various substances with each other to provide a setting mass which in set condition is adapted to fix prostheses at surrounding bone tissue, and whereby the mixture is applied to the bone tissue by means of a feed device (20) from which the mixture (19) may be pressed out. In order to avoid transfer of the mixture from a special mixing container to the feed device, the present device comprises an agitator (8) which is connectable to the feed device (20) and a vacuum source (17) which is connectable to the feed device for mixing said substances in said feed device under vacuum.

12 Claims, 4 Drawing Figures

METHOD FOR PRODUCING BONE CEMENT FOR FIXING PROSTHESES AND DEVICE FOR CARRYING OUT SAID METHOD

The present invention relates to a method for producing bone cement for fixing prostheses, whereby the bone cement is manufactured by mixing various substances with each other to provide a setting mass which in set condition is adapted to fix prostheses at surrounding bone tissue. The present invention also relates to a device for carrying out said method.

Bone cement is produced by mixing two or more substances with such properities that the mixture is set. Before setting the mixture has the character of a soft mass which is introduced into the bone tissue into which the prostheses shall be applied. When the mass is in position in the bone tissue, the prosthesis is inserted therein and fixed in position after setting of the bone cement.

When mixing the substances, substantial amounts of air are stirred into the mixture and it has been observed that the strength of the final product is more and more reduced with an increasing amount of air in the mixture.

The object of the present invention is to eliminate this problem and increase the strength of the final product. This is arrived at, according to the invention, by mixing the various substances during vacuum. The object of the invention is also to provide a suitable device for carrying out said method and such a device is characterized substantially by the fact that a feed device for delivering the mixture to the bone tissue is connectable to a mixing device and a vacuum source.

Since mixing occurs during vacuum, air supply to the mixture is minimized and since mixing may occur in the feed device, it is not necessary to transfer the mixture from a mixing bowl or similar to the feed device.

The invention will be further described below with reference to the accompanying drawings, in which FIG. 1 is a section through a device for mixing bone cement in accordance with the present method;

Figure 1:
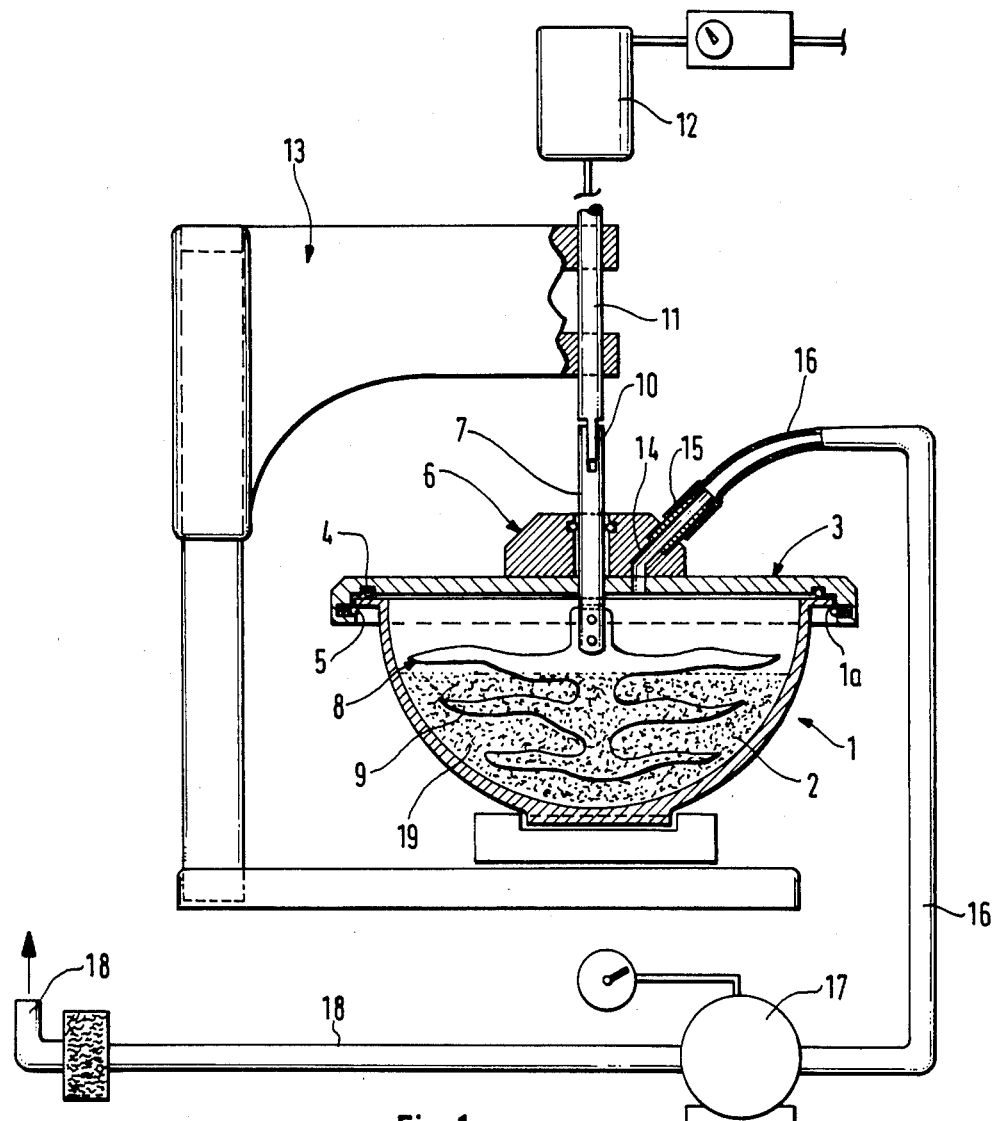

For carrying out the method according to the invention, a mixing container 1 is used, including a space 2 for mixing. The mixing container 1 may be provided with a cap 3, which may be sealingly connected to the mixing container by means of a sealing ring 4 or similar. The cap 3 is arranged on the mixing container 1 such that it adheres thereto and this holding may be obtained by means of resilient balls 5 provided on the cap 3 and gripping under an edge 1a on said mixing container 1.

The cap 3 comprises a mounting member 6, wherein the shaft 7 of an agitator 8 is rotably mounted. The agitator 8 comprises agitator blades 9 which are adapted to extend downwards close to the bottom of the mixing space 2. The shaft 7 of the agitator 8 has a recess 10 for permitting connection of the shaft 7 to an output shaft 11 of a driving motor 12 for operating the agitator 8. The driving motor 12 is mounted on a frame 13, onto which the mixing container 1 may be positioned for carrying out the mixing procedure.

The cap 3 and its mounting member 6 has a passage 14 and a connecting nipple 15 is provided on the mounting member 6, the interior of said nipple defining an extension of said passage 14. A hose 16 to a vacuum pump 17 is connectable to the connecting nipple 15 and said pump 17 is adapted to obtain a vacuum in the mixing space 2 by sucking out air therefrom through the passage 14, connecting nipple 15 and hose 16. The vacuum pump 17 is adapted to lead out air and gases from the mixing space 2 via an outlet conduit 18 and also from the operating room wherein the mixing is carried out.

For the manufacture of bone cement, two or more suitable substances are placed in the space 2 of the mixing container 1. Of these substances, one substance is a liquid, substantially including monomethylmethacrylate, and another substance, a powder, substantially consisting of polymethylmethacrylate.

By mixing said substances and eventual additional substances of suitable type, a mixture 19 is obtained which is set to an acrylate-based bone cement.

Figure 2:
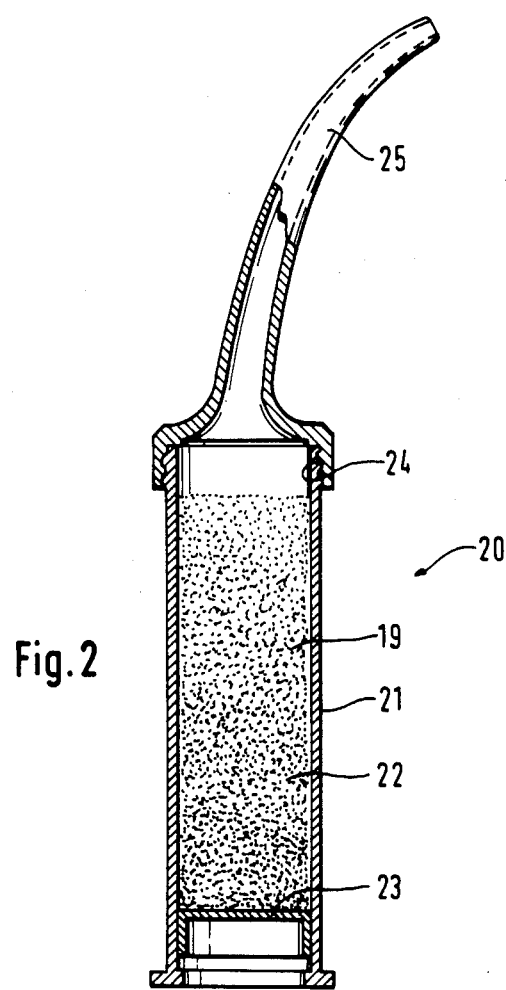
FIG. 2 is a section through a feed device for delivering bone cement to bone tissue.
Figure 4:
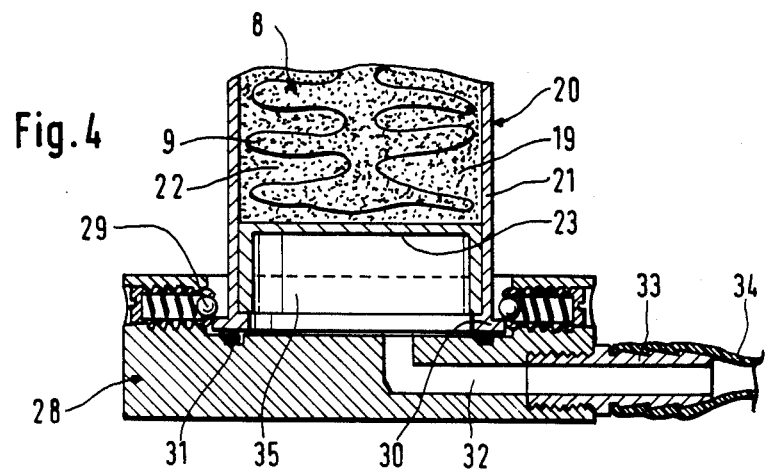
FIG. 4 is a section through the lower portion of the device of FIG. 3.

In order to obtain said mixture 19, said liquid is poured into the space 2 of the mixing container 1. Eventually, the liquid may be cooled to 2°-6° C., preferably 4° C., before or after supplying it to the mixing space 2 in order to facilitate the mixing procedure and/or improve the properties of the final product. After supplying the liquid to the mixing space 2, the powder is added to said liquid. The cap 3 is placed on the mixing container 1 and the container on the frame 13, whereby the agitator shaft 7 is connected to the drive shaft 11. Thereafter, the hose 16 from the vacuum pump 17 is connected to the connecting nipple 15 and the pump is activated. The vacuum pump 17 is operated a certain time, e.g. at least 5 seconds, preferably at least 10 seconds, until a vacuum of at least 70%, preferably 90-98%, is generated in the mixing space 2. It is generally suitable to generate by means of the vacuum pump 17 a vacuum (negative pressure) of 0,05-0,5 bar absolute pressure and carry out the mixing at this vacuum. When the desired vacuum is generated, the agitator 8 is activated to rotate and because of this stirring, the substances in the space 2 will mix under vacuum to a suitable mixture 19. While the mixing procedure is carried out under vacuum, addition of air into the mixture 19 during stirring is minimized. A minimum stirring time is required for efficient stirring of the mixture 19. This is e.g. 30-90 seconds, preferably 30-60 seconds. It may be advantageous to carry out the mixing procedure at a temperature of 0°-21° C. in the mixing space 2. After the required mixing, the vacuum is abolished and the mixture 19 obtained in the mixing space 2 is tranferred to a feed device 20 (see FIG. 2) adapted to deliver the mixture 19 to that cavity in the bone tissue wherein the prosthesis shall be fixed. The feed device 20 comprises a cylinder 21 defining a space 22 for the mixture 19 and provided with a displaceable piston 23. The cylinder 21 has a threaded end portion 24, onto which a discharge tube 25 is screwed. After filling of the mixture 19, the feed device 20 is placed in a discharging device (not shown) adapted to press out the mixture 19 via the discharge tube 25 by moving the piston 23 towards said tube. When the feed device 20 has been placed in the discharging device, the discharge tube 25 is bought into that cavity in the bone tissue wherein the prosthesis shall be fixed and a suitable amount of mixture is discharged from the feed device 20 by means of the discharging device. Thereafter, the prosthesis is inserted into the mixture 19 in the bone tissue and placed in the desired position, whereafter the mixture is setting. After setting, the bone cement fix the prosthesis in its position.

Figure 3:
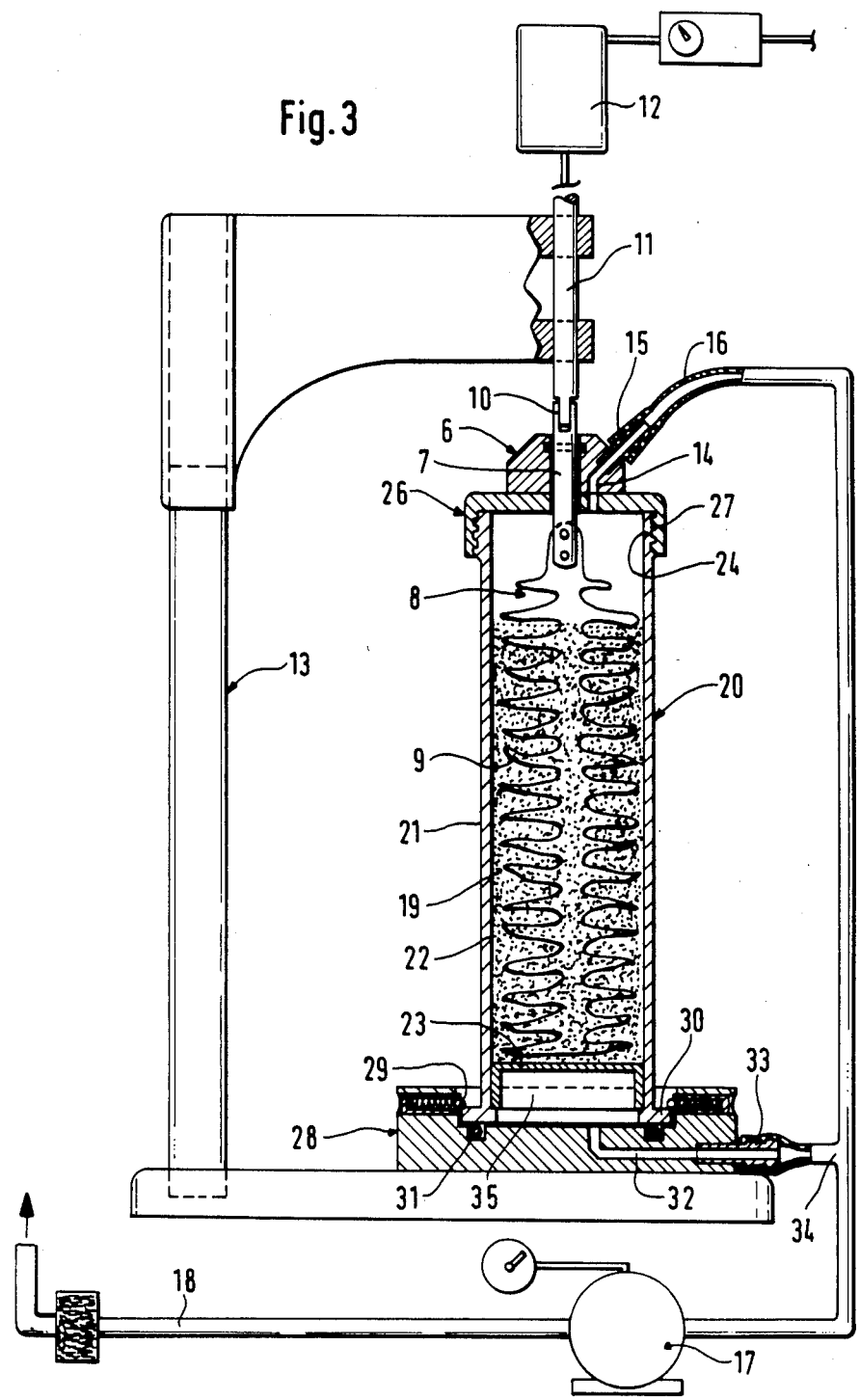
FIG. 3 is a section through another device for mixing bone cement as in the method according to the invention.

In order to avoid transfer of the mixture 19 from a mixing bowl to a feed device, the device of FIG. 3 may be used. Hereby, mixing of the mixture 19 occurs in the space 22 of the feed device 20. In that case, a cap 26 corresponding to the cap 3 is used, but it has threads 27 such that it may be screwed onto the threaded end portion 24 of the cylinder 21. In that case, the frame 13 is preferably provided with a holding device 28 adapted to hold the cylinder 21 of the feed device 20 during the mixing procedure with the agitator 8. The holding device 28 comprises spring loaded balls 29 which can snap over a lower collar 30 on the cylinder 21. The underside of the lower collar 30 engages the holding device 28 through a sealing ring 31. The holding device 28 has a passage 32 opening into a connecting nipple 33. A branch 34 of the hose 16 to the vacuum pump 17 is connectable to said nipple 33.

Liquid and powder of the abovementioned type is brought into the space 22 in the feed device 20, the cap 26 is screwed on, the feed device 20 is placed on the holding device 28 and the hoses 16, 34 are connected. Thereafter, the vacuum pump 17 is activated, which means that a vacuum is generated in the space 22 on one side of the piston 23 as well as in a space 25 beneath the piston. This means that the piston 23 will not be sucked upwards by a vacuum in the space 22, since there is a corresponding vacuum on the other side of the piston 23.

When stirring is finished, the cap 26 is loosened, the cylinder 21 is removed from the holding device 28 and the discharge tube 25 is screwed thereon, whereby the feed device 20 is ready for use with the discharging device. In this case it is thus ensured that the mixture 19 in no way is moved from one space to another before inserting it into the cavity in the bone tissue.

The invention is not limited to the described method nor the illustrated device, but may vary within the scope of the following claims. Thus, mixing may occur at another suitable vacuum than within the aforementioned values of 0,05-0,5 bar, the liquid need not necessarily be cooled to 2°-6° C., preferably about 4° C., but may be cooled to other temperatures or not be cooled at all, the mixing procedure may eventually occur at other temperatures than 0°-21° C. in the mixing space 2, the mixing procedure may begin at another occasion than the abovementioned and the mixing time may vary within other limits than the abovementioned. The bone cement may be produced by mixing other substances than the abovementioned and the mixing may occur in other types of containers and spaces than the aforementioned. Stirring of the mixture under vacuum may be carried out manually and other types of frames and vacuum generating devices than the abovementioned may eventually be used.

I claim:

1. Method for producing bone cement for fixing prostheses, whereby the bone cement is manufactured by mixing various substances with each other to provide a setting mass which in set condition is adapted to fix prostheses at surrounding bone tissue, characterized by mixing said various substances under vacuum of 0.05-0.5 bar absolute pressure and at temperatures within the range of 0°-21° C. in a mixing space (2) intended for the mixture in order to minimize addition of air into the mixture.

2. Method according to claim 1, whereby one of the substances in the mixture is a liquid, e.g. monomethylmethacrylate, characterized by cooling said liquid before mixing to a temperature of 2°-6° C.

3. Method according to claim 1, characterized by initiating mixing after a certain vacuum has been obtained in a mixing container (1) adapted for mixing.

4. Method according to claim 1, whereby mixing is carried out in an operating room wherein the bone is operated, and whereby vacuum is generated by means of a vacuum source (17) which is connectable to a mixing container (1 or 21) wherein mixing occurs, characterized by discharging gases generated in the mixing container (1 or 21) before and/or during and/or after mixing by means of the vacuum source (17).

5. The method for producing bone cement for fixing prostheses according to claim 1 whereby the bone cement is manufactured by mixing various substances with each other to provide a setting mass which in set condition is adapted to fix prostheses at surrounding bone tissue, and whereby the mixture is applied to the bone tissue by means of a feed device (20) from which the mixture (19) may be pressed out, characterized by an agitator (8) which is connectable to the feed device (20) and by a vacuum source (17) which is connectable to the feed device for mixing said substances in said feed device under vacuum characterized further in that the agitator (8) and vacuum source (17) are connectable to the feed device (20) through a cap (26) for sealing off a space (22) in said feed device, from which space the mixture (19) is intended to be pressed out.

6. Device according to claim 5, whereby the feed device (20) comprises a displaceable piston (23) which is adapted to be moved into a space (22) with the mixture (19) for pressing out the mixture therefrom and whereby mixing of said mixture occurs in said space while said space is connected to the vacuum source (17) for generating a vacuum in said space, characterized in that the vacuum source (17) is provided also to subject a space (35) on the outside of the piston (23) to vacuum while it at the same time generates vacuum in the space (22) within the piston, whereby the space (35) is defined by the outer side of the piston and by a holding device (28) for holding the feed device (20) during the mixing procedure.

7. Method for producing bone cement for fixing prostheses, whereby the bone cement is manufactured by mixing various substances with each other to provide a setting mass which in set condition is adapted to fix prostheses at surrounding bone tissue, and whereby the various substances are mixed under vacuum in a feed device (20) and the mixture is applied to the bone tissue by pressing out said mixture by means of a piston (23), characterized by generating generally equal vacuums inside the feed device (20) and in a space (35) outside the piston (23).

8. Method according to claim 7, whereby one of the substances in the mixture is a liquid, monomethylmethacrylate, characterized by cooling said liquid before mixing to a temperature of 2°-6° C.

9. A method for producing bone cement, comprising the steps:
placing ingredients of bone cement in a container, said container including a movable plunger;
mixing the ingredients placed in the container;
during said mixing step, inducing a vacuum on opposing sides of said plunger; and after said mixing step, urging contents from said container by moving said plunger.

10. the method according to claim 9, wherein said placing step includes the step of partially filling the container with the ingredients on one side of said plunger so as to leave a first space in said container, said inducing step including the steps of defining a second space on an opposite side of said plunger and evacuating said first and second spaces simultaneously.

11. A device for producing bone cement, comprising:
container means for receiving ingredients of a bone cement, said container means including movable plunger means for urging contents from said container;
means for mixing ingredients received in said container; and
means for inducing a vacuum upon opposing sides of said plunger means during operation of said mixing means.

12. The device according to claim 11, wherein said vacuum inducing means comprises:
means for evacuating a space within said container means;
means for defining a second space located on an opposite side of said plunger means from said container space; and
means for evacuating said second space simultaneously with evacuation of said container space.

* * * * *